US012787964B2

(12) United States Patent
Tillman

(10) Patent No.: US 12,787,964 B2
(45) Date of Patent: Nov. 10, 2026

(54) PEANUT VARIETY 'ARNIE'

(71) Applicant: University of Florida Research Foundation, Inc., Gainesville, FL (US)

(72) Inventor: Barry Tillman, Marianna, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 289 days.

(21) Appl. No.: 18/646,037

(22) Filed: Apr. 25, 2024

(65) Prior Publication Data

US 2025/0331484 A1 Oct. 30, 2025

(51) Int. Cl.
*A01H 6/54* (2018.01)
*A01H 5/10* (2018.01)

(52) U.S. Cl.
CPC ............... *A01H 6/541* (2018.05); *A01H 5/10* (2013.01)

(58) Field of Classification Search
None
See application file for complete search history.

(56) References Cited

U.S. PATENT DOCUMENTS 8,178,752 B1 5/2012 Tillman et al.
11,197,449 B2 * 12/2021 Branch .................... A01H 5/10

OTHER PUBLICATIONS

Branch, W.D. "Registration of 'Georgia Greener' peanut." Journal of Plant Registrations 1:121, (2007).
Branch, et al. "Uniform peanut performance tests 2013." Office of Communication, University of Georgia, Coastal Plain Experiment Station, Research Progress Report No. 4-14. 28 pages. Apr. 2014.
Tillman, B. "Registration of 'FloRun '331" peanut." Journal of Plant Registrations, 15(2), 294-299, (2021).
Culbreath, et al. "High levels of field resistance to tomato spotted wilt virus in peanut breeding lines derived from hypogea and hirsute botanical varieties." Peanut Science, 32, 20-24, (2005).
Tillman. "'Arnie'—A New Peanut Variety Released by the University of Florida." University of Florida, IFAS Extension, (2024). Retrieved from <https://nwdistrict.ifas.ufl.edu/phag/2024/02/02/arnie-a-new-peanut-variety-released- by-the-university-of-florida/>.
Karthik, et al. "Genotype-independent and enhanced in planta Agrobacterium tumefaciens-mediated genetic transformation of peanut [*Arachis hypogaea* (L.)]." 3 Biotech. 8(4):202, (2018).
Brown, et al. "Development of a method of risk assessment to facilitate integrated management of spotted wilt of peanut." Plant Disease, 89(4), 348-356, (2005).

* cited by examiner

*Primary Examiner* — Vinod Kumar
(74) *Attorney, Agent, or Firm* — Dentons US LLP

(57) ABSTRACT

The invention provides plants of the peanut variety designated 'Arnie'. The invention thus relates to the plants, cells, plant parts, and tissue cultures of the variety 'Arnie', and to methods for producing a peanut plant produced by crossing a peanut plant of variety 'Arnie' with another peanut plant, such as a plant of another variety. The invention further relates to peanut seeds and plants produced by crossing plants of variety 'Arnie' with plants of another variety. The invention further relates to the genetic complements and hybrid genetic complements of plants of variety 'Arnie'.

21 Claims, 9 Drawing Sheets

2020 Crop Relative Index of All Varieties vs. Georgia 06G Control

Sample Set: University of Florida

| Relative Index Varieties | Control GA-06G | UF11X02-HO1-14-1-2 | UF11X02-HO2-20-1-2 | UF11X23-3-6-1 | 14X078-HO4-2-1-1 | 14X067-HO2-7-1-1 | 14X070-HO2-2-1-1 | 14X098-HO4-12-1-1 |
|---|---|---|---|---|---|---|---|---|
| **Chemical Data** | | | | | | | | |
| Fat Content - % | 49.2 | 50.0 | 49.4 | 49.9 | 49.0 | 47.5 | 50.3 | 48.1 |
| Relative Index | | [illegible] | [illegible] | [illegible] | [illegible] | [illegible] | [illegible] | [illegible] |
| Sugar Content - % | 4.1 | 3.5 | 3.9 | 3.8 | 4.0 | 3.6 | 3.1 | 3.3 |
| Relative Index | | [illegible] | [illegible] | [illegible] | [illegible] | [illegible] | [illegible] | [illegible] |
| Protein Content - % | 22.5 | 21.8 | 21.3 | 20.4 | 22.8 | 22.8 | 22.2 | 24.3 |
| Relative Index | | [illegible] | [illegible] | [illegible] | [illegible] | [illegible] | [illegible] | [illegible] |
| **Shelf-Life Indicators** | | | | | | | | |
| Peroxide Value - meq/Kg | 0.1 | 0.4 | 0.2 | 0.4 | 0.3 | 0.3 | 0.3 | 0.4 |
| Relative Index | | [illegible] | [illegible] | [illegible] | [illegible] | [illegible] | [illegible] | [illegible] |
| Free Fatty Acids - % | 0.1 | 0.2 | 0.2 | 0.1 | 0.1 | 0.3 | 0.1 | 0.1 |
| Relative Index | | [illegible] | [illegible] | [illegible] | [illegible] | [illegible] | [illegible] | [illegible] |
| O/L Ratio | 2.0 | 7.0 | 28.8 | 32.6 | 2.4 | 29.3 | 39.2 | 25.2 |
| Relative Index | | [illegible] | [illegible] | [illegible] | [illegible] | [illegible] | [illegible] | [illegible] |
| **Physical Data** | | | | | | | | |
| Roast Variability - % | 8.8 | 5.6 | 7.8 | 7.8 | 1.3 | 9.8 | 9.3 | 8.3 |
| Relative Index | | [illegible] | [illegible] | [illegible] | [illegible] | [illegible] | [illegible] | [illegible] |
| Blanched (wholes+splits) - % | 93.3 | 93.6 | 98.8 | 98.3 | 88.0 | 94.3 | 88.4 | 95.5 |
| Relative Index | | [illegible] | [illegible] | [illegible] | [illegible] | [illegible] | [illegible] | [illegible] |
| Red Nose - Unblanched - % | 6.7 | 6.4 | 3.5 | 0.7 | 12.1 | 5.8 | 11.7 | 4.8 |
| Relative Index | | [illegible] | [illegible] | [illegible] | [illegible] | [illegible] | [illegible] | [illegible] |
| Seed Size (% Med) | 27.5 | 40.9 | 40.5 | 36.1 | 20.8 | 38.4 | 32.7 | 41.8 |
| Relative Index | | [illegible] | [illegible] | [illegible] | [illegible] | [illegible] | [illegible] | [illegible] |
| Flavor (Roasted Peanut) | 4.3 | 5.0 | 5.6 | 6.2 | 4.5 | 5.4 | 5.0 | 5.2 |
| Relative Index | | [illegible] | [illegible] | [illegible] | [illegible] | [illegible] | [illegible] | [illegible] |

FIG. 3

| **2022 Leaf spot test Marianna, FL** | No Sprays | | 4 Sprays | | 8 Sprays | | Average | |
|---|---|---|---|---|---|---|---|---|
| | Leaf spot | Pod Yield | Leaf spot | Pod Yield | Leaf spot | Pod Yield | Leaf spot | Pod Yield |
| Genotype | 1-10 | lbs./A | 1-10 | lbs./A | 1-10 | lbs./A | 1-10 | lbs./A |
| FloRun™ '331' | 7.8 | 5302 | 5.3 | 5482 | 2.8 | 6621 | 5.3 | 5802 |
| FloRun™ '52N' | 4.5 | 5739 | 4.0 | 5376 | 1.5 | 5269 | 3.3 | 5461 |
| FloRun™ 'T61' | 9.0 | 4185 | 5.5 | 5066 | 2.8 | 6099 | 5.8 | 5117 |
| Georgia-06G | 7.0 | 4746 | 5.0 | 6038 | 2.8 | 6316 | 4.9 | 5700 |
| Georgia-12Y | 5.0 | 5984 | 4.3 | 6207 | 2.5 | 6566 | 3.9 | 6253 |
| TifNV-High O/L | 7.0 | 5590 | 4.3 | 6181 | 2.0 | 6997 | 4.4 | 6256 |
| TUFRunner™ '297' | 9.3 | 4056 | 6.5 | 5919 | 3.0 | 6418 | 6.3 | 5464 |
| UF14x070-HO4-2-1-1 | 7.0 | 3600 | 4.8 | 5011 | 2.3 | 6900 | 4.7 | 5277 |
| LSD | Interaction not significant | | | | | | 0.78 | 863 |

| **2023 Leaf spot test Marianna, FL** | No Sprays | | 4 Sprays | | 8 Sprays | | Average | |
|---|---|---|---|---|---|---|---|---|
| | Leaf spot | Pod Yield | Leaf spot | Pod Yield | Leaf spot | Pod Yield | Leaf spot | Pod Yield |
| Genotype | 1-10 | lbs./A | 1-10 | lbs./A | 1-10 | lbs./A | 1-10 | lbs./A |
| FloRun™ '52N' | 8.3 | 5352 | 2.8 | 6567 | 2.0 | 6157 | 4.3 | 6025 |
| FloRun™ 'T61' | 9.0 | 3894 | 5.5 | 7289 | 2.0 | 8374 | 5.5 | 6519 |
| Georgia-12Y | 4.5 | 7259 | 2.3 | 8222 | 1.5 | 8229 | 2.8 | 7903 |
| Georgia-20VHO | 8.0 | 4701 | 2.8 | 7371 | 1.3 | 6755 | 4.0 | 6275 |
| TifNV-HG | 7.5 | 6265 | 2.5 | 6697 | 1.8 | 8053 | 3.9 | 7005 |
| UF14x070-HO4-2-1-1 | 8.0 | 5644 | 2.5 | 8036 | 1.8 | 6925 | 4.1 | 6868 |
| LSD | Interaction not significant | | | | | | 0.73 | 860 |

FIG. 4

| 2023 - Marianna, FL | Yield (lbs/acre) | | | | White Mold Rating (1-10) | | |
|---|---|---|---|---|---|---|---|
| name | Inoculated | Not Inoculated | Loss | Mean | Inoculated | Not Inoculated | Mean |
| 15x084-HO1-1-SSD-19 | 1173 | 7870 | 6696 | 4522 | 9.7 | 1.0 | 5.3 |
| FloRun™ '52N' | 1768 | 5196 | 3428 | 3482 | 9.3 | 2.0 | 5.7 |
| FloRun™ 'T61' | 1588 | 7033 | 5445 | 4311 | 9.2 | 1.3 | 5.3 |
| Georgia-12Y | 2223 | 6143 | 3920 | 4183 | 8.2 | 1.2 | 4.7 |
| Georgia-20VHO | 895 | 6542 | 5647 | 3719 | 9.3 | 1.7 | 5.5 |
| TifNV-HG | 839 | 6241 | 5401 | 3540 | 9.8 | 1.5 | 5.7 |
| UF14x070-HO4-2-1-1 | 712 | 6661 | 5949 | 3687 | 9.8 | 1.3 | 5.6 |
| **LSD (P<0.05):** | **901** | | | **225** | **1.0** | | **0.4** |

| 2023- Tifton, GA | White Mold | | | | | |
|---|---|---|---|---|---|---|
| Genotypes | % zeros | No Zeros | All | TSWV | LS | Yield |
| 21. 14X070-HO4-2-1-1 | 0.0 | 55.8 | 60.1 | 2.5 | 2.3 | 4682 |
| 41. TifNV-HG | 8.3 | 53.6 | 50.7 | 16.7 | 2.4 | 5656 |
| 42. TifNV-High O/L | 16.7 | 28.0 | 23.1 | 16.7 | 2.6 | 6065 |
| 43. GA-06G | 0.0 | 42.5 | 42.5 | 39.1 | 3.4 | 4903 |
| 45. TUFRunner 297 | . | . | . | 33.3 | 3.3 | 4533 |
| 46. GA-20VHO | 0.0 | 70.8 | 70.8 | 11.7 | 3.0 | 4184 |
| 49. Florun T61 | 33.3 | 32.8 | 22.7 | 13.3 | 3.3 | 6638 |
| 52. GA-12Y | 20.8 | 33.0 | 27.8 | 7.5 | 3.1 | 6045 |
| LSD(P<0.05) | 12.5 | 20.9 | 19.4 | 17.6 | 0.7 | 1310 |

FIG. 5

Clemson, SC, Dr. Dan Anco yield trial dug 134 DAP.

| Genotype | TSWV incidence | Grouping | Yield (lb/A) | Grouping |
|---|---|---|---|---|
| UF14x070-HO4-2-1-1 | 2.8% | d | 4414 | a |
| UF14x068-HO3-14-1-1 | 9.2% | abcd | 4337 | a |
| 15x092-HO1-3-1-1 | 4.8% | cd | 3936 | ab |
| Georgia 16HO | 15.3% | abc | 3910 | ab |
| UF11x27-1-14-1-1 | 10.0% | abcd | 3902 | ab |
| TUFRunner 297 | 5.7% | bcd | 3883 | ab |
| UF11x23-3-6-1-1 | 18.2% | ab | 3576 | ab |
| FloRun 331 | 17.4% | ab | 3342 | b |
| Georgia 06G | 19.8% | a | 3254 | b |

FIG. 6

Clemson, SC, Dr. Dan Anco yield trial dug 150 DAP.

| Genotype | TSWV incidence | Grouping | Yield (lb/A) | Grouping |
|---|---|---|---|---|
| UF11x27-1-14-1-1 | 12.3% | cdef | 5596 | a |
| UF14x068-HO3-14-1-1 | 6.1% | fgh | 5198 | ab |
| UF14x070-HO4-2-1-1 | 4.4% | gh | 5176 | ab |
| FloRun T61 | 14.6% | abcde | 5151 | abc |
| Georgia 16HO | 15.4% | abcd | 5086 | abc |
| UF11x23-3-6-1-1 | 23.4% | a | 5076 | abc |
| Georgia 12Y | 13.3% | bcdef | 5029 | abc |
| 15x092-HO1-3-1-1 | 4.0% | h | 5000 | abc |
| TUFRunner 297 | 13.0% | bcdef | 4986 | abc |
| TifNV-HG | 13.2% | bcdef | 4834 | abcd |
| Georgia 06G | 20.0% | abc | 4756 | abcd |
| Georgia 21GR | 22.9% | ab | 4720 | abcd |
| Georgia 20VHO | 7.3% | efgh | 4590 | bcd |
| FloRun 52N | 13.6% | abcde | 4386 | bcd |
| TifNV-High O/L | 12.9% | cdef | 4322 | cd |
| AU NPL 17 | 10.6% | defg | 4116 | d |
| FloRun 331 | 21.6% | abc | 4071 | d |

FIG. 7

Clemson, SC, Dr. Dan Anco yield trial sprayed with Bravo fungicide 3 times.

| Genotype | TSWV incidence | Grouping | LLS incidence | Grouping | LLS defoliation | Grouping | Yield lb/A | Grouping |
|---|---|---|---|---|---|---|---|---|
| Bailey II | 2.2% | cdef | 54.80% | a | 0.80% | ab | 5268 | a |
| UF 11x23-3-6-1-1 | 2.0% | cdef | 41.20% | a | 0.40% | b | 5213 | a |
| UF 14x070-HO4-2-1-1 | 1.2% | ef | 44.30% | a | 0.40% | b | 5189 | a |
| FR 331 | 6.5% | abcd | 38.00% | a | 0.40% | b | 5117 | a |
| Emery | 6.2% | abcd | 64.00% | a | 0.70% | ab | 4926 | a |
| Comrade | 7.3% | abc | 68.40% | a | 2.10% | a | 4911 | a |
| NC-20 | 0.9% | f | 50.60% | a | 0.80% | ab | 4838 | a |
| 15x092-HO1-3-1-1 | 1.2% | ef | 29.20% | a | 0.40% | b | 4830 | a |
| UF 14x068-HO3-14-1-1 | 2.4% | bcdef | 25.10% | a | 0.40% | b | 4780 | a |
| Walton | 8.3% | ab | 62.50% | a | 0.40% | b | 4709 | a |
| Ga 21GR | 9.0% | a | 23.60% | a | 0.40% | b | 4596 | a |
| TifNV-HG | 2.6% | bcdef | 55.40% | a | 0.40% | b | 4567 | a |
| UF 11x27-1-14-1-1 | 1.8% | def | 51.30% | a | 0.40% | b | 4533 | a |
| Ga 12Y | 4.9% | abcde | 64.10% | a | 0.40% | b | 4409 | a |
| FR T61 | 1.4% | ef | 61.40% | a | 0.40% | b | 4363 | a |
| AU 17 | 7.0% | abc | 63.20% | a | 0.40% | b | 4252 | a |
| TifJumbo | 4.2% | abcde | 68.50% | a | 0.40% | b | 4251 | a |
| Ga 20VHO | 2.4% | bcdef | 32.30% | a | 0.40% | b | 4235 | a |
| FR 52N | 2.0% | cdef | 20.10% | a | 0.40% | b | 4101 | a |
| AU Barkley | 1.2% | ef | 18.20% | a | 0.40% | b | 4099 | a |
| TR 511 | 5.8% | abcd | 32.30% | a | 0.40% | b | 4084 | a |
| Ga 18HP | 2.6% | bcdef | 57.90% | a | 0.40% | b | 3956 | a |

FIG. 8

PEANUT VARIETY 'ARNIE'

BACKGROUND OF THE INVENTION

Field of the Invention

The present invention relates to the field of plant breeding and, more specifically, to peanut plants having an oleic oil profile suitable for peanut butter production, medium seed size, excellent disease resistance, high pod yield, and high percentage of total sound mature kernels (TSMK). In particular, the invention relates to plants and seeds of the variety designated as 'Arnie', and derivatives and tissue cultures thereof.

Description of Related Art

Peanut, *Arachis hypogaea*, is an important oilseed crop grown mainly for its edible seeds. Peanut plants are cultivated in over 100 countries worldwide. Most of peanut production in the United States has traditionally been located in the southeast (e.g. Alabama, Florida, Georgia), southwest (e.g. New Mexico, Oklahoma, Texas), and in North Carolina and Virginia. The United States currently produces about 10% of the world's peanut crop and ranks third in peanut production behind China and India. Peanut varieties are valued for high yields, nutritional quality, as well as resistance to biotic and abiotic stresses.

In peanuts, Tomato Spotted Wilt Virus (TSWV) stunts plants, reduces yield, and causes shriveled, misshapen pods. TSWV has become widely distributed across the southeastern United States and is currently a severely limiting factor in peanut production. TSWV was first observed in Texas in 1971. TSWV was responsible for up to 50% yield loss in southern Texas in the late 1980s; and caused significant losses in Georgia in the late 1990s. Although TSWV-related losses began to slowly decline in the 2000s due to the adoption of effective control measures, recent epidemics of TSWV in Texas, Mississippi, and Georgia show that the virus is still a serious threat to peanut production. Peanuts planted early in the growing season (e.g. before May 1st) are the most at risk for TSWV infection, with the highest levels of TSWV generally seen in peanuts planted in early to mid-April.

The most noticeable symptoms on affected peanut plants are stunting, yellowing of foliage (chlorosis) and characteristic "ring spots" on the leaves. Symptoms of TSWV infection may also include discolored hulls and kernels, dwarfed pod size, leaf curling, decreased pod number and size, and often death of the plant. Initial symptoms usually appear a few weeks after planting, and newly affected plants continue to appear throughout the rest of the growing season.

TSWV continues to be one of the most common and most damaging diseases to peanuts in the United States. Although varieties having some resistant to TSWV, such as Georgia Green, have been introduced to the market, there is a continuing need to develop new TSWV resistant varieties. Moreover, peanut varieties having high TSWV resistance in combination with additional agronomically desirable traits are of significant commercial interest.

SUMMARY OF THE INVENTION

In one aspect, the invention provides peanut plants and seeds of variety 'Arnie'. Also provided are seeds and plants having all of the physiological and morphological characteristics of variety 'Arnie'. Parts of these peanut plants are also provided, for example, including a seed, a cutting, a stem, a leaf, an axillary bud, a flower, pollen, or an ovule.

In another aspect of the invention, a tissue culture of regenerable cells of peanut variety 'Arnie' is provided. The tissue culture will preferably be capable of regenerating peanut plants capable of expressing all of the physiological and morphological characteristics of the starting plant and of regenerating plants having substantially the same genotype as the starting plant. Examples of some of the physiological and morphological characteristics of peanut variety 'Arnie' include those traits set forth in the phenotypic description provided herein. The regenerable cells in such tissue culture may be derived, for example, from a stem, a leaf, an axillary bud, a flower, pollen, or an ovule. Still further, the present invention provides peanut plants regenerated from a tissue culture of the invention, the plants having all of the physiological and morphological characteristics of peanut variety 'Arnie'.

In yet another aspect, the invention provides a method of vegetatively propagating a peanut plant comprising the steps of: (a) collecting tissue capable of being propagated from a plant of peanut variety 'Arnie'; and (b) propagating a plant from said tissue. The method will preferably be capable of producing peanut plants capable of expressing all of the physiological and morphological characteristics of the starting plant and of producing plants having substantially the same genotype as the starting plant. Still further, the present invention provides peanut plants produced by vegetative propagation of peanut variety 'Arnie'. In some embodiments, such plants have all of the physiological and morphological characteristics of peanut variety 'Arnie'.

In one aspect, the present invention provides a method of introducing a trait into a peanut plant, the method comprising the steps of: (a) utilizing as a recurrent parent a plant of peanut variety 'Arnie' by crossing the plant with a donor peanut plant that comprises a trait to produce $F_1$ progeny; (b) selecting an $F_1$ progeny that comprises the trait; (c) backcrossing the selected $F_1$ progeny with a plant of variety 'Arnie' to produce backcross progeny; and (d) selecting a backcross progeny comprising the trait and the morphological and physiological characteristics of the recurrent parent peanut variety used in step (a); and (e) repeating steps (c) and (d) three or more times to produce a selected fourth or higher backcross progeny that comprises the trait. In some embodiments, plants produced by such methods are also provided.

In one aspect, a plant of peanut variety 'Arnie' further comprising an added heritable trait is provided. In some embodiments, the heritable trait may comprise a transgene or may comprise a genetic locus that is, for example, a dominant or recessive allele. In specific embodiments, the added genetic locus may confer one or more traits, such as for example, herbicide tolerance, insect resistance, pest resistance, disease resistance, and environmental stress tolerance. In further embodiments, the trait may be conferred by a naturally occurring gene introduced into the genome of a line by backcrossing, a non-transgenic mutation, or a transgene introduced through genetic transformation techniques into the plant or a progenitor of any previous generation thereof. When introduced through transformation, a genetic locus may comprise one or more genes integrated at a single chromosomal location.

In another aspect, a plant of peanut variety 'Arnie' further comprising a single locus conversion is provided. In some embodiments, a single locus conversion includes one or more site-specific changes to the plant genome, such as, without limitation, one or more nucleotide modifications, deletions, or insertions. A single locus may comprise one or more genes or nucleotides integrated or mutated at a single chromosomal location. In one embodiment, a single locus conversion may be introduced by a genetic engineering technique, methods of which include, for example, genome editing with engineered nucleases (GEEN). Engineered nucleases include, but are not limited to, Cas endonucleases; zinc finger nucleases (ZFNs); transcription activator-like effector nucleases (TALENs); engineered meganucleases, also known as homing endonucleases; and other endonucleases for DNA or RNA-guided genome editing that are well-known to the skilled artisan. The single locus conversion may confer one or more traits, such as for example, herbicide tolerance, insect resistance, pest resistance, disease resistance, and environmental stress tolerance.

In yet another aspect, the invention provides a method comprising applying plant breeding techniques to a plant of peanut variety 'Arnie'. In some embodiments, the method comprises producing a peanut variety 'Arnie'-derived peanut plant. Non-limiting examples of plant breeding techniques include recurrent selection, mass selection, hybridization, open-pollination, backcrossing, modified backcrossing, pedigree breeding, mutation breeding, or marker assisted selection. In one embodiment, the method comprises selecting a peanut variety 'Arnie'-derived peanut plant that comprises the normal oleic acid profile, high yield, high grade, or TSWV resistance found in peanut variety 'Arnie'. In specific embodiments, a peanut plant produced by the breeding techniques described herein may have a normal oleic acid profile, high yield, high grade, or TSWV resistance.

In still yet another aspect, the present invention provides a method of producing a seed of a peanut variety 'Arnie'-derived peanut plant, the method comprising the steps of: (a) producing a peanut variety 'Arnie'-derived peanut plant from a seed produced by crossing a plant of peanut variety 'Arnie' with itself or a second peanut plant; and (b) crossing the peanut variety 'Arnie'-derived peanut plant with itself or a different peanut plant to obtain a seed of a further peanut variety 'Arnie'-derived peanut plant. In some embodiments, the method further comprises repeating the producing and crossing steps of (a) and (b) using the seed from step (b) for producing a plant according to step (a) for at least one generation to produce a seed of an additional peanut variety 'Arnie'-derived peanut plant.

Any embodiment discussed herein with respect to one aspect of the invention applies to other aspects of the invention as well, unless specifically noted.

The term "about" is used to indicate that a value includes the standard deviation of the mean for the device or method being employed to determine the value. The use of the term "or" in the claims is used to mean "and/or" unless explicitly indicated to refer to alternatives only or the alternatives are mutually exclusive. When used in conjunction with the word "comprising" or other open language in the claims, the words "a" and "an" denote "one or more," unless specifically noted otherwise. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits.

Other objects, features, and advantages of the present invention will become apparent from the following detailed description. It should be understood, however, that the detailed description and any specific examples provided, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 3: Shows the 2020 Crop Relative Index of UF14x070-HO4-2-1-1 (also known as 'Arnie') and other experimental varieties as compared to Georgia-06G UF14x070-HO4-2-1-1 is shown to have an O/L Ratio of 2.4, whereas Georgia-06G is shown to have an O/L Ratio of 2.0.

FIG. 4: Shows tolerance of UF14x070-HO4-2-1-1 (also known as 'Arnie') to late leaf spot, caused by *Cercosporidium* personatum, as compared to other commercial varieties in Florida.

FIG. 5: Shows tolerance of UF14x070-HO4-2-1-1 (also known as 'Arnie') to white mold, caused by Scelrotium *rolfsii*, as compared to other commercial varieties in Florida.

FIG. 6: Shows results of yield trial conducted in Clemson, SC, dug 134 days after planting, for UF14x070-HO4-2-1-1 (also known as 'Arnie') as compared to other experimental and commercial varieties.

FIG. 7: Shows results of yield trial conducted in Clemson, SC, dug 150 days after planting, for UF14x070-HO4-2-1-1 (also known as 'Arnie') as compared to other experimental and commercial varieties.

FIG. 8: Shows results of yield trial (sprayed with Bravo fungicide 3 times) conducted in Clemson, SC for UF14x070-HO4-2-1-1 (also known as 'Arnie') as compared to other experimental and commercial varieties.

DETAILED DESCRIPTION OF THE INVENTION

Definitions

Figure 1:
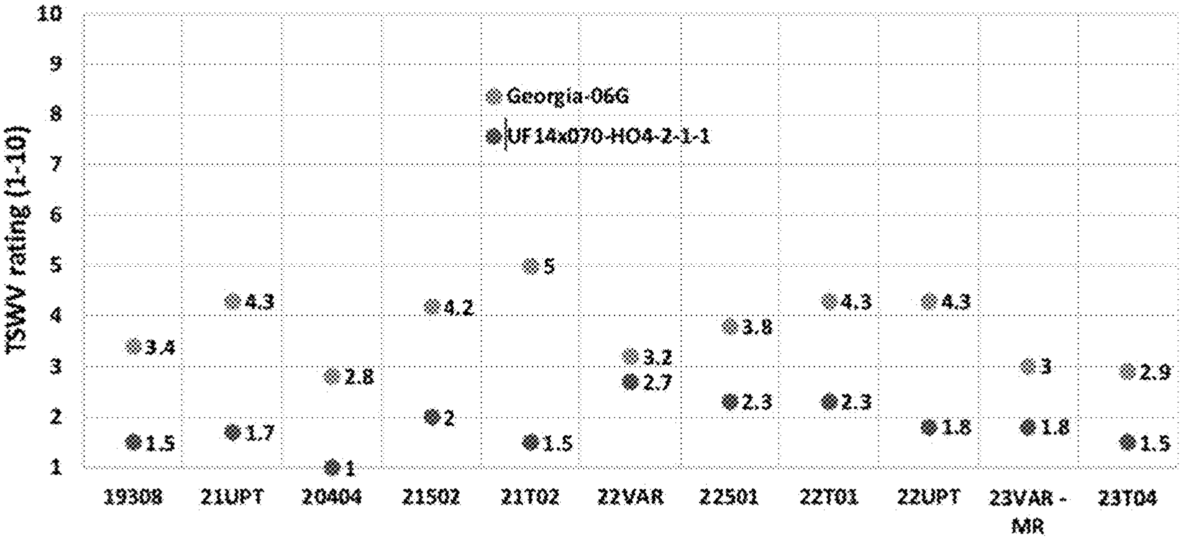
FIG. 1: Shows the TSWV rating of peanut variety Georgia-06G and UF14x070-HO4-2-1-1 (also known as 'Arnie') calculated from four years (including 11 TSWV isolate tests) of TSWV evaluations carried out in Marianna, FL. The average rating of Georgia-06G was 3.8, whereas the average rating of UF14x070-HO4-2-1-1 was 1.8, a statistically significant difference of 2.0 on a scale of 1 to 10.
Figure 2:
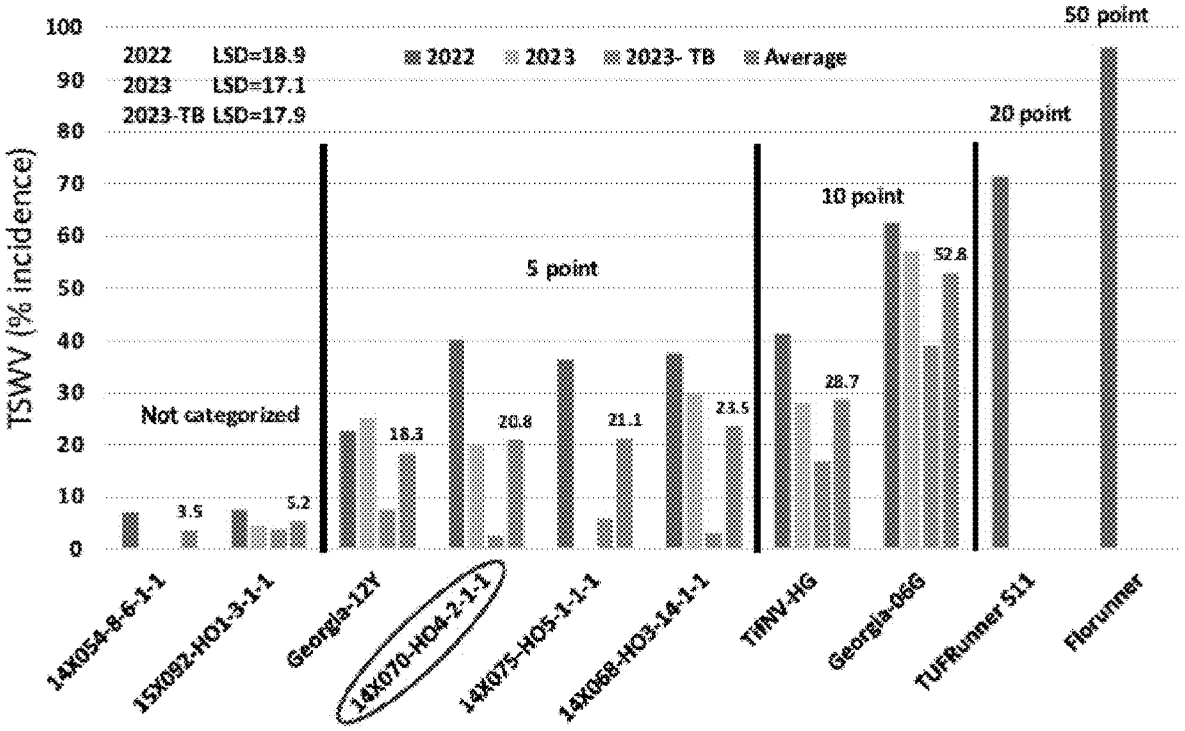
FIG. 2: Shows the TSWV incidence of peanut variety UF14x070-HO4-2-1-1 (also known as 'Arnie') as compared to other commercial and experimental varieties from evaluations carried out in Tifton, GA. UF14x070-HO4-2-1-1 is shown to be in the 5 category based on the PeanutRx scale by comparing the TSWV incidence to Georgia-12Y, which is in the 5 category (2024 Peanut Rx Interactive Analysis Tool). This places 'Arnie' into the lowest current TSWV risk category and provides growers more flexibility in managing TSWV disease.

Allele: Any of one or more alternative forms of a gene locus, all of which alleles relate to one trait or characteristic. In a diploid cell or organism, the two alleles of a given gene occupy corresponding loci on a pair of homologous chromosomes.

Backcrossing: A process in which a breeder repeatedly crosses hybrid progeny back to one of the parents, for example, a first generation hybrid ($F_1$) with one of the parental genotypes of the $F_1$ hybrid.

Crossing: The pollination of a female flower of a peanut plant, thereby resulting in the production of seed from the flower.

Cross-pollination: Fertilization by the union of two gametes from different plants.

Diploid: A cell or organism having two sets of chromosomes.

Tetraploid: A cell or organism having four sets of chromosomes.

$F_1$ Hybrid: The first generation progeny of the cross of two plants.

Flower: Refers to all parts of the flower, including but not limited to, stigma, style, ovary, anther, filament, corolla, and calyx.

Genetic Complement: An aggregate of nucleotide sequences, the expression of which sequences defines the phenotype in peanut plants, or components of plants including cells or tissue.

Genotype: The genetic constitution of a cell or organism.

Haploid: A cell or organism having one set of the two sets of chromosomes in a diploid.

Linkage: A phenomenon wherein alleles on the same chromosome tend to segregate together more often than expected by chance if their transmission was independent.

Marker: A readily detectable phenotype, preferably inherited in codominant fashion (both alleles at a locus in a diploid heterozygote are readily detectable), with no environmental variance component, i.e., heritability of 1.

Maturity date: The evaluation of plants considered as mature when the highest percentage of the pods have reached the mature colors, black, brown, and orange.

Non-transgenic mutation: A mutation that is naturally occurring (spontaneous), or induced by conventional methods (e.g. exposure of plants to radiation or mutagenic compounds), not including mutations made using recombinant DNA techniques.

Phenotype: The detectable characteristics of a cell or organism in which the characteristics are the manifestation of gene expression.

Peanut flour: Flour high in protein, often used as a gluten-free solution.

Peanut oil: Oil having a mild flavor, high smoke point, and high monounsaturated content.

Pod: Refers to the fruit of a peanut plant. It consists of the hull or shell (pericarp) and the peanut seeds.

Quantitative Trait Loci (QTL): Genetic loci that contribute, at least in part, certain numerically representable traits that are usually continuously distributed.

Regeneration: The development of a plant from tissue culture.

SSR profile: A profile of simple sequence repeats used as genetic markers and scored by gel electrophoresis following PCR amplification using flanking oligonucleotide primers.

Self-pollination: The transfer of pollen from the anther to the stigma of the same plant.

Single Locus Converted (Conversion) Plant: Plants that are developed by a plant breeding technique called backcrossing or by genetic engineering of a locus, wherein essentially all of the morphological and physiological characteristics of a plant are recovered in addition to the characteristics conferred by the single locus transferred into the plant via the backcrossing or genetic engineering technique.

Substantially Equivalent: A characteristic that, when compared, does not show a statistically significant difference (e.g., p=0.05) from the mean.

Tissue Culture: A composition comprising isolated cells of the same or a different type or a collection of such cells organized into parts of a plant.

Tomato Spotted Wilt Virus (TSWV): A spherical negative-sense RNA virus within the family Bunyaviridae. TSWV, which is commonly transmitted by *thrips*, causes serious losses in economically important crops and it is one of the most economically devastating plant viruses in the world.

Transgene: A genetic sequence that has been introduced into the nuclear or chloroplast genome of a peanut plant by genetic transformation or site-specific modification.

*ARACHIS hypogaea* Variety 'Arnie'

Provided herein are methods and compositions relating to plants, seeds, and derivatives of peanut variety 'Arnie'. This variety shows uniformity and stability within the limits of environmental influence for the traits described hereinafter. In particular, peanut variety 'Arnie' exhibits high yield, a high grade (TSMK), an oleic acid profile suitable for peanut butter production, and significant TSWV resistance.

A. Origin and Breeding History

Peanut variety 'Arnie' was developed using a pedigree breeding system. The original developmental cross was made in a greenhouse at the North Florida Research and Education Center near Marianna, Florida in 2014 using line 08x46-2-10-1-1 as the female parent and line UF13303 as the male parent.

The female parent, 08x46-2-10-1-1, is a breeding line resulting from a 2008 cross between UF Georgia Greener and breeding line 02x26-1-B2-1-1-4. Georgia Greener (Branch, 2007) is a medium seeded, normal oleic, runner type, with disease resistance to spotted wilt virus released in 2006 by the Georgia Agricultural Experiment Stations. The male parent, UF13303, is an advanced, high oleic, medium seed size, breeding line from the University of Florida that originates from a 2007 cross between two UF breeding lines.

Six F1 seeds from the 2014 cross between the breeding line 08x46-2-10-1-1 and the breeding line UF13303 were planted in the field in Marianna, Florida in 2015. Pedigree selection was practiced in the F2, F3, and F4 generations with one generation sown each year. In 2016, F2 seeds from five F1:2 plants were sown in the field in Marianna, Florida, and a total of five F2:3 plants were selected from F1:2 plant number four based on pod size. In 2017 a single F3:4 plant was selected for inclusion preliminary yield tests. The F4 plant formed the line designated 14x070-HO4-2-1-1 which was tested during 2018, 2019, 2020, 2021, 2022 and 2023. In 2021, the experimental designation UF14x070-HO4-2-1-1 was assigned. UF14x070-HO4-2-1-1 was given variety designation 'Arnie'. A summary of the breeding history is provided in Table 1.

TABLE 1

| Summary of the breeding history of UF14x070-HO4-2-1-1 | | | | | | | |
|---|---|---|---|---|---|---|---|
| Selection | Pedigree | Fn | Year | Test | Location | Breeding Method | Disease Tests |
| UF14x070-HO4-2-1-1 | 08x46-2-10-1-1/UF13303 | 9 (Bulk) | 2023 | 23VAR | MR, GV, LO, JY | Bulk | 23L01, 23W01, 23T01 |
| UF14x070-HO4-2-1-1 | | 8 (bulk) | 2022 | 22501, 22UPT, 22VAR | MR, GV, LO, JY | Bulk | 22L01, 22W01, 22T01 |
| UF14x070-HO4-2-1-1 | | 7 (bulk) | 2021 | 21UPT, 21502 | MR, GV, JY | Bulk | 21L02, 21W02, 21T02 |
| UF14x070-HO4-2-1-1 | | 6 (bulk) | 2020 | 20404 | MR | Bulk | |
| UF14x070-HO4-2-1-1 | | 5 | 2019 | 19308 | MR | Bulk | — |
| UF14x070-HO4-2-1-1 | | 4 | 2018 | 18B05, 18221 | MR | Pedigree | — |
| 14x070-HO4-2-1 | | 3 | 2017 | 17B13 | MR | Pedigree | |
| 14x070-HO4-2 | | 2 | 2016 | 16B18 | MR | Pedigree | |
| 14x070-HO4 | | 1 | 2015 | 15F1s | MR | Pedigree | |
| 14x070 | | | 2014 | Cross | MR | Pedigree | |

Between 2019 and 2023, 'Arnie's oleic oil profile, yield, grade, seed size, and tolerance to leaf spot, white mold, and TSWV were evaluated in Florida, Georgia, and/or South Carolina (See, e.g. FIGS. 1-8). In brief, 'Arnie' comprises an oleic oil profile suitable for peanut butter production (i.e. normal), small runner seed size (700-750 sound mature kernels (SMK) per pound; ~38% mediums), greater yield in Florida as compared to Georgia-06G, similar yield to Flo-Run™ 331, excellent TSMK (75-77% TSMK), excellent resistance to TSWV, and similar tolerance to leaf spot and white mold as compared to Georgia-06G. 'Arnie' has also been shown to produce smaller seeds and more medium kernels as compared to Georgia-06G. In 2022, 23,000 lbs. of breeder seed was produced. In 2023, about 90 A of foundation seed was planted, and a total of about 950,000 pounds of seed (in shell) was harvested. The plants massed in 2022 and 2023 were uniform and stable. No variants or off types were observed in either the breeders seed increase or the foundation seed increase.

B. Phenotypic Description

In accordance with another aspect of the present invention, there is provided a peanut plant having the morphological characteristics of peanut variety 'Arnie'. A description of the morphological and physiological characteristics of peanut plant 'Arnie' is presented in Tables 2 and 3, and FIGS. 1-9.

The following characteristics have been repeatedly observed and can be used to distinguish 'Arnie' as a new and distinct variety of *Arachis hypogaea* plant:

1. Normal oleic oil profile suitable for peanut butter production;
2. Medium seed size;
3. High pod yield;
4. Propensity for 3-celled pods
5. High grade; and
6. Significant TSWV resistance.

'Arnie' has not been observed under all possible environmental conditions. Phenotype may vary due to environmental influence without variation in genotype. Peanut variety 'Arnie' shows uniformity and stability within the limits of environmental influence for the traits described herein, such as the characteristics noted in Tables 2 and 3, and FIGS. 1-9. No variant traits have been observed or are expected in 'Arnie'.

TABLE 2

| Yield, Grade and Seed Size of 'Arnie' compared to Georgia-06G; 2019-2023, Florida | | | | | | | |
|---|---|---|---|---|---|---|---|
| Trait | No. Tests | Georgia-06G | 'Arnie' | % Control | Variance | (t) | Significance |
| Mediums (%) | 5 | 26.1 | 37.9 | 144.9 | 23.6 | −2.6 | ++ |
| Oleic (%) | 1 | 57.4 | 53.1 | 92.5 | 0.8 | 1.0 | NS |
| HSW (g) | 5 | 72.8 | 64.6 | 88.8 | 10.5 | 2.8 | −− |
| TSMK (%) | 6 | 77.9 | 78.8 | 101.2 | 0.8 | −2.0 | + |
| TSWV (1-10) | 16 | 2.3 | 1.5 | 63.8 | 0.8 | 3.8 | −−− |
| Yield (lbs./A) | 23 | 6080 | 6788 | 111.6 | 955397 | −3.7 | +++ |

+++, ++, + are significantly greater by paired t-test at p <= 1%, 5% and 10%, respectively.

−−−, −−, − are significantly less by paired t-test at p <= 1%, 5% and 10%, respectively.

TABLE 3

| Yield, Grade and Seed Size of 'Arnie' compared to FloRun 52N; 2019-2023, Florida | | | | | | | |
|---|---|---|---|---|---|---|---|
| Trait | No. Tests | FloRun 52N | 'Arnie' | % Control | Variance | (t) | Significance |
| Mediums (%) | 3 | 34.9 | 38.5 | 110.4 | 20.5 | −0.6 | NS |
| HSW (g) | 3 | 62.8 | 64.2 | 102.1 | 5.2 | −0.4 | NS |
| TSMK (%) | 7 | 77.5 | 77.5 | 100.0 | 0.97 | 0.53 | NS |
| TSWV (1-10) | 10 | 2.6 | 1.6 | 60.1 | 0.95 | 2.7 | -- |
| Yield (lbs./A) | 16 | 6644 | 6948 | 105.1 | 712076 | −1.6 | NS |

+++, ++, + are significantly greater by paired t-test at p <= 1%, 5% and 10%, respectively.
---, --, - are significantly less by paired t-test at p <= 1%, 5% and 10%, respectively.

C. Deposit Information

A deposit of representative sample of seed of peanut variety 'Arnie' was made with the the Provasoli-Guillard National Center for Marine Algae and Microbiota (NCMA), 60 Bigelow Drive, East Boothbay, Maine, 04544 USA. The deposit was assigned NCMA Accession No. 11202408002. The date of deposit of the representative sample of plant seed with the NCMA was Aug. 1, 2024. The deposit has been accepted under the Budapest Treaty and will be maintained in the NCMA depository for a period of 30 years, or 5 years after the most recent request, or for the enforceable life of the patent, whichever is longer, and will be replaced if necessary, during that period. Upon issuance, all restrictions on the availability to the public of the deposit will be irrevocably removed consistent with all of the requirements of the Budapest Treaty and 37 C.F.R. §§ 1.801-1.809. Applicant does not waive any infringement of rights granted under this patent or under the Plant Variety Protection Act (7 USC 2321 et seq.).

Further Embodiments of the Invention

A. Plant Breeding

In one aspect, the present disclosure provides plants modified using the methods described herein to include at least a first desired heritable trait. Such plants may, in one embodiment, be developed by backcrossing, wherein essentially all of the desired morphological and physiological characteristics of a variety are recovered in addition to a genetic locus transferred into the plant via the backcrossing technique. The term single locus converted plant as used herein refers to those plants which are developed by backcrossing or by genetic engineering, wherein essentially all of the desired morphological and physiological characteristics of a variety are recovered in addition to the single locus transferred into the variety via the backcrossing or genetic engineering technique, respectively. By essentially all of the desired morphological and physiological characteristics, it is meant that the characteristics of a plant are recovered that are otherwise present when compared in the same environment, other than an occasional variant trait that might arise during backcrossing, direct introduction of a transgene, or application of genetic engineering technique.

Backcrossing methods can be used with the present invention to improve or introduce a trait into a variety. The term backcrossing as used herein refers to the repeated crossing of a hybrid progeny back to one of the parental peanut plants. The parental peanut plant that contributes the locus or loci for the desired trait is termed the nonrecurrent or donor parent. This terminology refers to the fact that the nonrecurrent parent is used one time in the backcross protocol and therefore does not recur. The recurrent parent therefore provides the desired genetic background, while the choice of the particular nonrecurrent parent will depend on the purpose of the backcross. One of the major purposes is to add some commercially desirable trait to the plant. The exact backcrossing protocol will depend on the characteristic or trait being altered and the genetic distance between the recurrent and nonrecurrent parents. Although backcrossing methods are simplified when the characteristic being transferred is a dominant allele, a recessive allele, or an additive allele (between recessive and dominant) may also be transferred. In this instance it may be necessary to introduce a test of the progeny to determine if the desired characteristic has been successfully transferred. The backcross process may be accelerated by the use of genetic markers, such as SSR, RFLP, SNP or AFLP markers to identify plants with the greatest genetic complement from the recurrent parent.

Modified backcrossing may also be used with the plants provided herein. This technique uses different recurrent parents during the backcrossing. Modified backcrossing may be used to replace the original recurrent parent with a variety having certain more desirable characteristics or multiple parents may be used to obtain different desirable characteristics from each.

With the development of molecular markers associated with particular traits, it is possible to add additional traits into an established germ line, such as represented here, with the end result being substantially the same base germplasm with the addition of a new trait or traits. Molecular breeding, as described in Moose and Mumm, 2008 (*Plant Physiol.,* 147:969-977), for example, and elsewhere, provides a mechanism for integrating single or multiple traits or QTL into an elite line. This molecular breeding-facilitated movement of a trait or traits into an elite line may encompass incorporation of a particular genomic fragment associated with a particular trait of interest into the elite line by the mechanism of identification of the integrated genomic fragment with the use of flanking or associated marker assays. In the embodiment represented here, one, two, three or four genomic loci, for example, may be integrated into an elite line via this methodology. When this elite line containing the additional loci is further crossed with another parental elite line to produce hybrid offspring, it is possible to then incorporate at least eight separate additional loci into the hybrid. In one embodiment, each locus may confer a separate trait. In another embodiment, loci may need to be homozygous and exist in each parent line to confer a trait in the hybrid. In yet another embodiment, multiple loci may be combined to confer a single robust phenotype of a desired trait.

Many traits have been identified that are not regularly selected for in the development of a new variety but that can be improved by backcrossing techniques. A genetic locus conferring the traits may or may not be transgenic. Examples of such traits known to those of skill in the art include, but are not limited to, herbicide tolerance, disease resistance, pest resistance, modified phosphorus content, modified antioxidant content, modified essential seed amino acid content, modified fatty acid content, modified carbohydrate content, and modified peanut fiber content, modified oil content, modified protein content, or other improved nutritional qualities. These genes are generally inherited through the nucleus, but may be inherited through the cytoplasm.

Selection of peanut plants for breeding is not necessarily dependent on the phenotype of a plant and instead can be based on genetic investigations. For example, one can utilize a suitable genetic marker which is closely genetically linked to a trait of interest. One of these markers can be used to identify the presence or absence of a trait in the offspring of a particular cross and can be used in selection of progeny for continued breeding. This technique is commonly referred to as marker assisted selection. Any other type of genetic marker or other assay which is able to identify the relative presence or absence of a trait of interest in a plant can also be useful for breeding purposes. Procedures for marker assisted selection are well known in the art. Such methods will be of particular utility in the case of recessive traits and variable phenotypes, or where conventional assays may be more expensive, time consuming, or otherwise disadvantageous. In addition, marker assisted selection may be used to identify plants comprising desirable genotypes at the seed, seedling, or plant stage, to identify or assess the purity of a variety, to catalog the genetic diversity of a germplasm collection, and to monitor specific alleles or haplotypes within an established variety.

Types of genetic markers which could be used in accordance with the invention include, but are not necessarily limited to, Simple Sequence Length Polymorphisms (SSLPs) (Williams et al., *Nucleic Acids Res.,* 1 8:6531-6535, 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., *Science,* 280:1077-1082, 1998).

In particular embodiments of the invention, marker assisted selection is used to increase the efficiency of a backcrossing breeding scheme for producing a peanut line comprising a desired trait. This technique is commonly referred to as marker assisted backcrossing (MABC). This technique is well-known in the art and may involve, for example, the use of three or more levels of selection, including foreground selection to identity the presence of a desired locus, which may complement or replace phenotype screening protocols; recombinant selection to minimize linkage drag; and background selection to maximize recurrent parent genome recovery.

B. Breeding of Peanut Variety 'Arnie'

The development of new varieties using one or more starting varieties is well known in the art and encompassed by the disclosure. In accordance with the disclosure, novel varieties may be created by crossing a plant of the disclosure followed by multiple generations of breeding according to such well-known methods. New varieties may be created by crossing with any second plant. New varieties may be developed, for example, by applying a breeding technique to a plant of peanut variety 'Arnie'. Such breeding techniques are well-known in the art and include but are not limited to recurrent selection, mass selection, hybridization, open-pollination, backcrossing, modified backcrossing, pedigree breeding, mutation breeding, and marker assisted selection. "Mutation breeding" as used herein refers to a breeding technique comprising selecting a naturally occurring (spontaneous) mutation or inducing a mutation through means such as irradiation or chemical induction.

In selecting a second plant to cross with a plant of the disclosure, it will typically be preferred to choose those plants which either themselves exhibit one or more selected desirable characteristics or which exhibit the desired characteristic(s) when in hybrid combination. Once initial crosses have been made, selection takes place to produce new varieties. Examples of desirable traits may include, in specific embodiments, an oleic oil profile suitable for peanut butter production, medium seed size, high pod yield, high TSMK grade, shape and uniformity, pest and disease resistance, herbicide tolerance, and adaptability for soil and climate conditions. Consumer-driven traits are other traits that may be incorporated into new plants developed by this disclosure.

One aspect of the current disclosure therefore provides methods for producing a peanut plant comprising a desirable trait, e.g. an early flowering trait, an upright habit, large leaves, or downy mildew resistance, found in peanut plant of variety 'Arnie'. In certain embodiments, the method may comprise (a) producing an peanut variety 'Arnie'-derived peanut plant from a seed produced by crossing a plant of peanut variety 'Arnie' with itself or a second peanut plant; (b) crossing the peanut variety 'Arnie'-derived peanut plant with itself or a different peanut plant to obtain a seed of a further peanut variety 'Arnie'-derived peanut plant; (c) selecting a further peanut variety 'Arnie'-derived peanut plant that comprises the desirable trait; (d) repeating said producing, crossing, and selecting steps of (a), (b), and (c) using the seed of said step (b) for at least one generation to produce a seed an additional 'Arnie'-derived peanut plant; and (e) selecting an additional peanut variety 'Arnie'-derived peanut plant that comprising the desirable trait. In a particular embodiment, the second plant may be a peanut plant and the progeny seed may be planted and grown to produce fertile hybrid progeny plants. A plant in accordance with the disclosure may be used in such crosses as the female plant or the male plant.

In some embodiments, a peanut plant of variety 'Arnie' or progeny thereof can comprise a TSWV incidence of less than about 20%, less than about 15%, less than about 10%, less than about 9%, less than about 8%, less than about 7%, less than about 6%, less than about 5%, less than about 4%, less than about 3%, less than about 2%, or less than about 1%. A peanut plant of variety 'Arnie' or progeny thereof may also be described as having a TSWV rating of less than about 5, less than about 4, less than about 3, less than about 2.5, less than about 2, less than about 1.75, less than about 1.5, or less than about 1.25. In other embodiments, a peanut plant of variety 'Arnie' or progeny thereof can comprise a TSMK of at least 70%, at least 72%, at least 74%, at least 75%, at least 76%, at least 77%, at least 78%, at least 79%, or least 80%. In still other embodiments, a peanut plant of variety 'Arnie' or progeny thereof can comprise a yield of at least 4500 pounds/acre (lb/a), at least 4750 lb/a, at least 5000 lb/a, at least 5500 lb/a, at least 6000 lb/a, or at least 6500 lb/a. In certain embodiments, a peanut plant of variety 'Arnie' or progeny thereof can comprise a at least 5% 3-celled pods, at least 6% 3-celled pods, at least 7% 3-celled pods, at least 8% 3-celled pods, at least 9% 3-celled pods, at least 10% 3-celled pods, at least 12% 3-celled pods, at least 15%, or least 20% 3-celled pods.

The disclosure also provides methods of producing peanut plants derived from peanut variety 'Arnie'. The method may comprise (a) crossing a peanut plant of peanut variety 'Arnie' with itself or a second plant capable of being crossed thereto; and (b) collecting resulting seed. In one embodiment, the second plant may be a peanut plant. In some embodiments, the methods of the present disclosure may further comprise the step of (c) crossing a plant grown from said seed of step (b) with itself or a second plant at least one or more additional time(s) to yield additional seed. Plants, seeds, and plant parts produced from the methods described herein are also provided.

In certain embodiments, hybrid seeds may be produced using the methods of the present disclosure. A parent plant of such a seed may be a peanut plant of peanut variety 'Arnie'. In other embodiments, a plant as described herein may be either the male plant or the female plant in a given cross.

In accordance with the disclosure, any species of peanut may be used. In particular, *Arachis* species that may be useful include but are not limited to *A. h. fastigiata, A. h. hypogaea*, and the like.

C. Plants Derived by Genetic Engineering

Various genetic engineering technologies have been developed and may be used by those of skill in the art to introduce traits in plants. In certain aspects of the claimed invention, traits are introduced into peanut plants via altering or introducing a single genetic locus or transgene into the genome of a recited variety or progenitor thereof. Methods of genetic engineering to modify, delete, or insert genes and polynucleotides into the genomic DNA of plants are well-known in the art.

In specific embodiments of the invention, improved peanut varieties can be created through the site-specific modification of a plant genome. Methods of genetic engineering include, for example, utilizing sequence-specific nucleases such as zinc-finger nucleases (see, for example, U.S. Pat. Appl. Pub. No. 2011-0203012); engineered or native meganucleases; TALE-endonucleases (see, for example, U.S. Pat. Nos. 8,586,363 and 9,181,535); and RNA-guided endonucleases, such as those of the CRISPR/Cas systems (see, for example, U.S. Pat. Nos. 8,697,359 and 8,771,945 and U.S. Pat. Appl. Pub. No. 2014-0068797). One embodiment of the invention thus relates to utilizing a nuclease or any associated protein to carry out genome modification. This nuclease could be provided heterologously within donor template DNA for templated-genomic editing or in a separate molecule or vector. A recombinant DNA construct may also comprise a sequence encoding one or more guide RNAs to direct the nuclease to the site within the plant genome to be modified. Further methods for altering or introducing a single genetic locus include, for example, utilizing single-stranded oligonucleotides to introduce base pair modifications in a peanut plant genome (see, for example Sauer et al., *Plant Physiol,* 170 (4): 1917-1928, 2016).

Methods for site-directed alteration or introduction of a single genetic locus are well-known in the art and include those that utilize sequence-specific nucleases, such as the aforementioned, or complexes of proteins and guide-RNA that cut genomic DNA to produce a double-strand break (DSB) or nick at a genetic locus. As is well-understood in the art, during the process of repairing the DSB or nick introduced by the nuclease enzyme, a donor template, transgene, or expression cassette polynucleotide may become integrated into the genome at the site of the DSB or nick. The presence of homology arms in the DNA to be integrated may promote the adoption and targeting of the insertion sequence into the plant genome during the repair process through homologous recombination or non-homologous end joining (NHEJ).

In another embodiment of the invention, genetic transformation may be used to insert a selected transgene into a plant of the disclosure or may, alternatively, be used for the preparation of transgenes which can be introduced by backcrossing. Methods for the transformation of plants that are well known to those of skill in the art and applicable to many plant species include, but are not limited to, electroporation, microprojectile bombardment, *Agrobacterium*-mediated transformation, and direct DNA uptake by protoplasts. For example, Navet, et al., describes *Agrobacterium*-mediated transformation of *Arachis hypogaea* (L.) (Karthik S et al. Genotype-independent and enhanced in planta *Agrobacterium tumefaciens*-mediated genetic transformation of peanut [*Arachis hypogaea* (L.)]. 3 *Biotech.* 2018 April; 8 (4): 202).

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

An efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target cells. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large. Microprojectile bombardment techniques are widely applicable and may be used to transform virtually any plant species.

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium*, allowing for convenient manipulations. Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (U.S. Pat. No. 5,563,055, incorporated herein by reference in its entirety). Transformation of plant protoplasts also can be achieved using methods based on calcium phosphate precipitation, polyethylene glycol treatment, electroporation, and combinations of these treatments.

A number of promoters have utility for plant gene expression for any gene of interest including but not limited to selectable markers, scoreable markers, genes for pest and disease resistance, and any other gene of agronomic interest. Examples of constitutive promoters useful for driving gene expression in plants include, but are not limited to, the cauliflower mosaic virus (CaMV) P-35S promoter, which confers constitutive, high-level expression in most plant tissues, including monocots; a tandemly duplicated version of the CaMV 35S promoter, the enhanced 35S promoter (P-e35S) the nopaline synthase promoter, the octopine synthase promoter; and the figwort mosaic virus (P-FMV) promoter as described in U.S. Pat. No. 5,378,619 (incorporated herein by reference in its entirety), and an enhanced version of the FMV promoter (P-eFMV) where the promoter sequence of P-FMV is duplicated in tandem, the cauliflower mosaic virus 19S promoter, a sugarcane bacilliform virus promoter, a *commelina* yellow mottle virus promoter, and other plant DNA virus promoters known to express in plant cells.

A variety of plant gene promoters that are regulated in response to environmental, hormonal, chemical, and/or developmental signals can be used for expression of an operably linked gene in plant cells, including promoters regulated by (1) heat, (2) light (e.g., pearbcS-3A promoter; maize rbcS promoter; or chlorophyll a/b-binding protein promoter), (3) hormones, such as abscisic acid, (4) wounding (e.g., wunl); or (5) chemicals such as methyl jasmonate, salicylic acid, or Safener. It may also be advantageous to employ organ-specific promoters.

Exemplary nucleic acids which may be introduced to the plants of this disclosure include, for example, DNA sequences or genes from another species, or even genes or sequences which originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA, which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a plant of peanut variety 'Arnie'. Non-limiting examples of particular genes and corresponding phenotypes one may choose to introduce into a of the disclosure include one or more genes for insect tolerance, such as a *Bacillus thuringiensis* (B.t.) gene, pest tolerance such as genes for fungal disease control, herbicide tolerance such as genes conferring glyphosate tolerance, and genes for quality improvements such as environmental or stress tolerances, or any desirable changes in plant physiology, growth, development, morphology or plant product(s). For example, structural genes would include any gene that confers insect tolerance including but not limited to a *Bacillus* insect control protein gene as described in WO 99/31248, U.S. Pat. Nos. 5,689,052, 5,500,365, and 5,880,275, each of which are herein incorporated by reference in their entirety. In another embodiment, the structural gene can confer tolerance to the herbicide glyphosate as conferred by genes including, but not limited to *Agrobacterium* strain CP4 glyphosate resistant EPSPS gene (aroA: CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety.

Alternatively, the DNA coding sequences can affect these phenotypes by encoding a non-translatable RNA molecule that causes the targeted inhibition of expression of an endogenous gene, for example via antisense- or co-suppression-mediated mechanisms. The RNA could also be a catalytic RNA molecule (i.e., a ribozyme) engineered to cleave a desired endogenous mRNA product. Thus, any gene which produces a protein or mRNA which expresses a phenotype or morphology change of interest is useful for the practice of the present disclosure.

D. Genetic Complements

In another aspect of the invention, the genetic complement of the peanut plant variety designated 'Arnie' is provided. The phrase "genetic complement" is used to refer to the aggregate of nucleotide sequences, the expression of which sequences defines the phenotype of, in the present case, a peanut plant, or a cell or tissue of that plant. A genetic complement thus represents the genetic makeup of cell, tissue or plant, and a hybrid genetic complement represents the genetic makeup of a hybrid cell, tissue, or plant. The invention thus provides peanut plant cells that have a genetic complement in accordance with the peanut plant cells disclosed herein, and plants, seeds and diploid plants containing such cells.

Plant genetic complements may be assessed by genetic marker profiles, and by the expression of phenotypic traits that are characteristic of the expression of the genetic complement, e.g., isozyme typing profiles. It is understood that variety 'Arnie' could be identified by any of the many well-known techniques such as, for example, Simple Sequence Length Polymorphisms (SSLPs) (Williams et al., *Nucleic Acids Res.*, 18:6531-6535, 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., *Science,* 280:1077-1082, 1998).

In yet another aspect, the present invention provides hybrid genetic complements, as represented by peanut plant cells, tissues, plants, and seeds, formed by the combination of a haploid genetic complement of a peanut plant of the invention with a haploid genetic complement of the same or a different variety. In another aspect, the present invention provides a peanut plant regenerated from a tissue culture that comprises a hybrid genetic complement of this invention.

E. Additional Traits

Additional traits can be introduced into the peanut variety of the present invention. A non-limiting example of such a trait is a coding sequence that decreases RNA and/or protein levels. The decreased RNA and/or protein levels may be achieved through RNAi methods, such as those described in U.S. Pat. No. 6,506,559 to Fire and Mellow.

Another trait that may find use with the peanut variety of the invention is a sequence that allows for site-specific recombination. Examples of such sequences include the FRT sequence, used with the FLP recombinase (Zhu and Sadowski, *J. Biol. Chem.,* 270:23044-23054, 1995); and the LOX sequence, used with CRE recombinase (Sauer, *Mol. Cell. Biol.,* 7:2087-2096, 1987). The recombinase genes can be encoded at any location within the genome of the peanut plant, and are active in the hemizygous state.

It may also be desirable to make peanut plants more tolerant to or more easily transformed with *Agrobacterium tumefaciens*. Expression of p53 and iap, two baculovirus cell-death suppressor genes, inhibited tissue necrosis and DNA cleavage. Additional targets can include plant-encoded proteins that interact with the *Agrobacterium* Vir genes; enzymes involved in plant cell wall formation; and histones, histone acetyltransferases and histone deacetylases (reviewed in Gelvin, *Microbiology & Mol. Biol. Reviews,* 67:16-37, 2003).

F. Plants Comprising Non-Transgenic Mutations

In still yet another aspect, a plant of peanut variety designated 'Arnie', further comprising a non-transgenic mutation is provided. The phrase "non-transgenic mutation" is used herein to refer to a mutation that is naturally occurring (spontaneous), or induced by conventional methods (e.g. exposure of plants to radiation or mutagenic compounds), not including mutations made using recombinant DNA techniques. Various mutagenesis techniques have been developed and may be used by those of skill in the art to induce mutations in plants. Methods of mutagenesis may include, for example, exposure to irradiation, mutagenic compounds, extreme heat, or tissue culture conditions; long-term seed storage; and targeting induced local lesions in genomes (TILLING). In some embodiments, ionizing radiation may be produced by X-rays, gamma rays, neutrons, beta rays, or ultraviolet rays. Non-limiting examples of chemical mutagens include base analogues, antibiotics, alkylating agents, sodium azide, hydroxylamine, nitrous acid, methylnitrilsourea, and acridines. Methods of mutagenesis to modify, delete, or insert polynucleotides into the genomic DNA are well-known in the art.

In one aspect, improved peanut varieties may be created through mutation of the plant genome. In one embodiment, a plant of the peanut variety 'Arnie' may be subjected to a mutagenesis technique to create a population of mutant plants. Such mutant plants, for example, may comprise a mutation and otherwise comprise all of the physiological and morphological characteristics of peanut variety 'Arnie'. In particular embodiments, mutant plants may comprise a mutation and otherwise comprise all of the morphological and physiological characteristics of peanut variety 'Arnie'.

G. Tissue Cultures and In Vitro Regeneration of Peanut Plants

In another aspect, the invention relates to tissue cultures of the peanut plant designated 'Arnie'. As used herein, the term "tissue culture" indicates a composition comprising isolated cells of the same or a different type or a collection of such cells organized into parts of a plant. Exemplary types of tissue cultures are protoplasts, calli and plant cells that are intact in plants or parts of plants, such as embryos, meristems, cotyledons, pollen, leaves, anthers, roots, root tips, pistil, flower, seed, stems, and the like. In a preferred embodiment, the tissue culture comprises cells derived from immature tissues of these plant parts. Means for preparing and maintaining plant tissue cultures are well known in the art (Abbasi, et al., *In Vitro Cell Dev. Biol.-Plant,* 43:481-492, 2007, and Parsons, et al., *Pharm. Biol.,* 56 (1): 485-494, 2018, each incorporated herein by reference in their entirety).

In yet another aspect, compositions are provided comprising a cell of peanut variety 'Arnie' comprised in plant cell growth media. Plant cell growth media are well known to those of skill in the art. For example, Ozudogru, et al., describes a direct organogenesis protocol for *Arachis hypogaea*. (Establishment of Direct Organogenesis Protocol for *Arachis hypogaea* cv. Virginia in Liquid Medium by Temporary Immersion System (TIS). *Horticulturae* 2022, 8, 1129; specifically incorporated herein by reference). Plant cell growth media can provide adequate support for plant cells, including providing moisture and/or nutritional components.

H. Processes of Crossing Peanut Plants and the Peanut Plants Produced by Such Crosses The present invention provides processes of preparing novel peanut plants and peanut plants produced by such processes. In accordance with such a process, a first parent peanut plant may be crossed with a second parent peanut plant wherein at least one of the first and second peanut plants is the peanut plant 'Arnie'. One application of the process is in the production of $F_1$ hybrid plants. Another important aspect of this process is that it can be used for the development of novel varieties. For example, the peanut plant 'Arnie' could be crossed to any second plant, and the resulting hybrid progeny could be vegetatively propagated, or the hybrid progeny could be each selfed for about 5 to 7 or more generations, thereby providing a large number of distinct varieties. These varieties could then be crossed with other varieties and the resulting hybrid progeny analyzed for beneficial characteristics. In this way, novel varieties conferring desirable characteristics could be identified. "Vegetative propagation" as used herein refers to any form of asexual reproduction occurring in plants in which a new plant grows from a fragment of the parent plant. Non-limiting examples of vegetative propagation methods include tissue culture and division.

I. $F_1$ Hybrid Peanut Plant and Seed Production

One beneficial use of the instant peanut variety is in the production of hybrid seed. Any time the peanut plant 'Arnie' is crossed with another, different, peanut plant, a first generation ($F_1$) peanut hybrid plant is produced. As such, an $F_1$ hybrid peanut plant can be produced by crossing 'Arnie' with any second peanut plant. Essentially any other peanut plant can be used to produce a hybrid peanut plant having peanut plant 'Arnie' as one parent. All that is required is that the second plant be fertile, which peanut plants naturally are, and that the plant is not peanut variety 'Arnie'.

The goal of the process of producing an $F_1$ hybrid is to manipulate the genetic complement of peanut to generate new combinations of genes that interact to yield new or improved traits (phenotypic characteristics). If the alleles are the same at a locus, there is said to be homozygosity. If they are different, there is said to be heterozygosity. Hundreds of peanut varieties are known to those of skill in the art, any one of which could be crossed with peanut plant 'Arnie' to produce a hybrid plant.

When the peanut plant 'Arnie' is crossed with another peanut plant to yield a hybrid, it can serve as either the maternal or paternal plant. For many crosses, the outcome is the same regardless of the assigned sex of the parental plants. Depending on the seed production characteristics relative to a second parent in a hybrid cross, it may be desired to use one of the parental plants as the male or female parent. Seed coat characteristics can be preferable in one plant. Pollen can be shed better by one plant. Therefore, a decision to use one parent plant as a male or female may be made based on any such characteristics as is well known to those of skill in the art.

J. Development of Peanut Varieties

The development of new varieties using one or more starting varieties is well known in the art. In accordance with the invention, novel varieties may be created by crossing peanut variety 'Arnie' followed by vegetative propagation of selected plants. In certain embodiments, novel varieties may be created by crossing peanut variety 'Arnie' followed by multiple generations of breeding according to such well-known methods. New varieties may be created by crossing peanut variety 'Arnie' with any second plant. In selecting such a second plant to cross for the purpose of developing novel varieties, it may be desired to choose those plants that either themselves exhibit one or more selected desirable characteristics or exhibit the desired characteristic(s) when in hybrid combination. Examples of potentially desired characteristics include foliage quality, shape and uniformity, maturity date, seed yield, seed germination rate, seedling vigor, pest and disease resistance, and adaptability for soil and climate conditions.

Once initial crosses have been made with peanut variety 'Arnie', vegetative propagation or inbreeding takes place to produce new varieties. Inbreeding requires manipulation by human breeders. Even in the extremely unlikely event inbreeding rather than crossbreeding occurred in natural peanut, achievement of complete inbreeding cannot be expected in nature due to well-known deleterious effects of homozygosity and the large number of generations the plant would have to breed in isolation. The reason for the breeder to create inbred plants is to have a known reservoir of genes whose gametic transmission is predictable.

The pedigree breeding method involves crossing two genotypes. Each genotype can have one or more desirable characteristics lacking in the other; or each genotype can complement the other. If the two original parental genotypes do not provide all of the desired characteristics, other genotypes can be included in the breeding population. Superior plants that are the products of these crosses are selfed and selected in successive generations. Each succeeding generation becomes more homogeneous as a result of self-pollination and selection. Typically, this method of breeding involves five or more generations of selfing and selection: $S_1 \rightarrow S_2$; $S_2 \rightarrow S_3$; $S_3 \rightarrow S_4$; $S_4 \rightarrow S_5$, etc. After at least five generations, the inbred plant is considered genetically pure.

Uniform lines of new varieties may also be developed by way of double-haploids. This technique allows the creation of true breeding lines without the need for multiple generations of selfing and selection. In this manner true breeding lines can be produced in as little as one generation. Haploid induction systems have been developed for various plants to produce haploid tissues, plants, and seeds. The haploid induction system can produce haploid plants from any genotype by crossing with an inducer line. Inducer lines and methods for obtaining haploid plants are known in the art.

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLES

Figure 9:
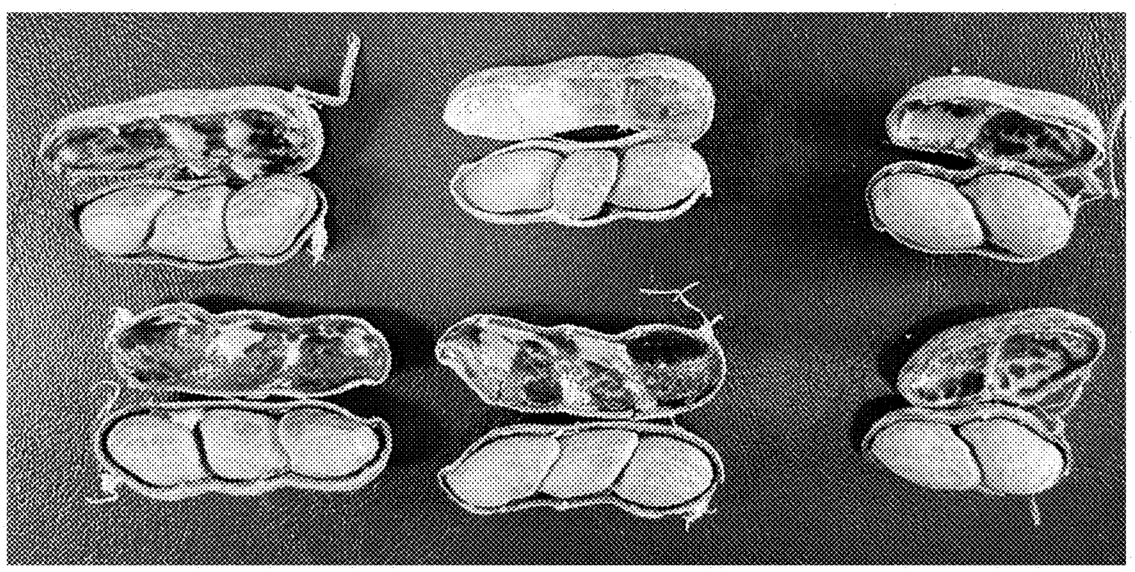
FIG. 9: Shows an example of two and three-celled pods of UF14x070-HO4-2-1-1.

Example 1-Distinguishing Characteristics of Peanut variety 'Arnie' Compared to Most Similar Variety The most distinguishing characteristics of peanut variety 'Arnie' include excellent TSWV resistance, pod yield, and competitive grade. 'Arnie' (UF14x070-HO4-2-1-1) is most similar to the FloRun™ '331' (Tillman, 2021). Both varieties have moderate seed size, high yield potential, and moderate resistance to white mold (*S. rolfsii*). One of the distinguishing features of UF14x070-HO4-2-1-1 as compared to FloRun™ '331' is its propensity for 3-celled pods compared to the typical runner which has a vast majority of 2-celled pods (Table 4). In four tests over two years, UF14x070-HO4-2-1-1 had between 12% and 22.5% 3-celled pods compared to between 0% and 1.3% for FloRun™ '331'. On average UF14x070-HO4-2-1-1 had 15% 3-celled pods compared to only 0.5% 3-celled pods for FloRun™ '331'. An example of the two and three-celled pods with seeds is shown in FIG. 9.

TABLE 4

Comparison of the percentage of three-celled pods in UF11x02-HO1-14-1-2 and FloRun ™ '331'.

| Genotype | 2022 | | 2023 | | |
|---|---|---|---|---|---|
| | 22501 | 22VAR | 23FFSP | 23MSI5 | Overall |
| | % pods with three cells | | | | |
| 14x070-H04-2-1-1 | 12.7 | 12.0 | 22.5 | 12.8 | 15 |
| FloRun 331 | 0.0 | 0.7 | 1.3 | 0.0 | 0.5 |
| Sig. (P < t) | 0.0581 | 0.0034 | 0.0027 | 0.0072 | <.0001 |

All of the compositions and methods disclosed and claimed herein can be made and executed without undue experimentation in light of the present disclosure. While the compositions and methods of this invention have been described in terms of the foregoing illustrative embodiments, it will be apparent to those of skill in the art that variations, changes, modifications, and alterations may be applied to the composition, methods, and in the steps or in the sequence of steps of the methods described herein, without departing from the true concept, spirit, and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

The references cited herein, to the extent that they provide exemplary procedural or other details supplementary to those set forth herein, are specifically incorporated herein by reference.

What is claimed is:

1. A peanut plant of variety 'Arnie', a representative sample of seed of the variety having been deposited under NCMA Accession No. 202408002.

2. A seed of peanut variety 'Arnie', a representative sample of seed of the variety having been deposited under NCMA Accession No. 2408002.

3. A plant part of the plant of claim 1, wherein the plant part comprises a cell of the plant.

4. The plant part of claim 3, defined as a seed, cutting, stem, leaf, axillary bud, flower, pollen, or ovule.

5. A peanut plant having all of the physiological and morphological characteristics of the plant of claim 1.

6. A tissue culture of regenerable cells of the plant of claim 1.

7. A peanut plant regenerated from the tissue culture of claim 6, wherein said regenerated peanut plant has all of the physiological and morphological characteristics of peanut variety 'Arnie', a representative sample of seed of the variety 'Arnie' having been deposited under NCMA Accession No. 202408002.

8. A method of vegetatively propagating the plant of claim 1, the method comprising the steps of:

(a) collecting a tissue capable of being propagated from the plant of claim 1; and (b) propagating a peanut plant from the tissue.

9. A method of introducing a trait into a peanut plant, the method comprising:

(a) utilizing as a recurrent parent the plant of claim 1 by crossing the plant with a donor peanut plant that comprises a trait to produce $F_1$ progeny;

(b) selecting an $F_1$ progeny that comprises the trait;

(c) backcrossing the selected $F_1$ progeny with a plant of the same peanut variety used as the recurrent parent in step (a) to produce backcross progeny;

(d) selecting a backcross progeny comprising the trait and otherwise comprising all of the morphological and physiological characteristics of the recurrent parent peanut variety used in step (a); and (e) repeating steps (c) and (d) three or more times to produce a selected fourth or higher backcross progeny.

10. A peanut plant produced by the method of claim 9, wherein the peanut plant produced by said method comprises the trait and otherwise comprises all of the morphological and physiological characteristics of peanut variety 'Arnie', and a representative sample of seed of the variety 'Arnie' having been deposited under NCMA Accession No. 202408002.

11. A method of producing a peanut plant comprising an added trait, the method comprising introducing a transgene conferring the added trait into the plant of claim 1, wherein the peanut plant produced by said method comprises the added trait and otherwise comprises all of the morphological and physiological characteristics of peanut variety 'Arnie', and a representative sample of seed of the variety 'Arnie' having been deposited under NCMA Accession No. 202408002.

12. A peanut plant produced by the method of claim 11.

13. The plant of claim 1, further comprising a transgene.

14. The plant of claim 13, wherein the transgene confers a trait selected from the group consisting of herbicide tolerance, insect resistance, pest resistance, disease resistance, and environmental stress tolerance.

15. The plant of claim 1, further comprising a single locus conversion.

16. The plant of claim 15, wherein the single locus conversion confers a trait selected from the group consisting of herbicide tolerance, insect resistance, pest resistance, disease resistance, and environmental stress tolerance.

17. A method of plant breeding comprising applying a plant breeding technique to a plant according to claim 1, wherein said plant breeding technique comprises recurrent selection, mass selection, hybridization, open-pollination, backcrossing, modified backcrossing, pedigree breeding, mutation breeding, or marker assisted selection.

18. The method of claim 17, further comprising producing a peanut variety 'Arnie'-derived peanut plant, a representative sample of seed of the variety 'Arnie' having been deposited under NCMA Accession No. 202408002.

19. The method of claim 17, further defined as comprising selecting a peanut variety 'Arnie'-derived peanut plant that comprises a normal oleic acid profile, high yield, high grade, or TSWV resistance found in peanut plant of variety 'Arnie', a representative sample of seed of the variety 'Arnie' having been deposited under NCMA Accession No. 202408002.

20. A method of producing a seed of a peanut variety 'Arnie'-derived peanut plant, the method comprising the steps of:

(a) producing a peanut variety 'Arnie'-derived peanut plant from a seed produced by crossing a plant of claim 1 with itself or a second peanut plant; and (b) crossing the peanut variety 'Arnie'-derived peanut plant with itself or a different peanut plant to obtain a seed of a further peanut variety 'Arnie'-derived peanut plant.

21. The method of claim 20, the method further comprising repeating the producing and crossing steps of (a) and (b) using the seed from step (b) for producing a plant according to step (a) for at least one generation to produce a seed of an additional peanut variety 'Arnie'-derived peanut plant.

* * * * *